United States Patent [19]

Gillessen et al.

[11] 4,066,635

[45] Jan. 3, 1978

[54] L-PYROGLUTAMYL-L-HISTIDYL-L-PROLYL-BETA-ALANINAMIDE AND SALTS

[75] Inventors: Dieter Gillessen, Birsfelden; Rolf Studer, Bottmingen, both of Switzerland; Arnold Trzeciak, Lorrach, Germany

[73] Assignee: Hoffmann-La Roche Inc., Nutley, N.J.

[21] Appl. No.: 724,796

[22] Filed: Sept. 20, 1976

Related U.S. Application Data

[63] Continuation of Ser. No. 603,405, Aug. 11, 1975, abandoned.

[51] Int. Cl.$^2$ .................... C07C 103/52; H61K 37/00
[52] U.S. Cl. .............................. 260/112.5 R; 424/177
[58] Field of Search .................. 260/112.5 R; 424/177

[56] References Cited

U.S. PATENT DOCUMENTS

| 3,651,039 | 3/1972 | Fujino et al. | 260/112.5 R |
| 3,876,624 | 4/1975 | McGregor | 424/177 |

OTHER PUBLICATIONS

Chem. Abst. 80, (1974), p. 143450j.
Chem. Abst. 81, (1974), p. 121006n.
J. Biol. Chem., 249, (1974), pp. 3085–3090.
Endocrinology, 95, (1974), pp. 978–983.

*Primary Examiner*—Delbert R. Phillips
*Attorney, Agent, or Firm*—Samuel L. Welt; George M. Gould

[57] ABSTRACT

This disclosure relates to L-pyroglutamyl-L-histidyl-L-prolyl-beta-alaninamide and acid addition salts thereof as anti-depressant agents.

6 Claims, No Drawings

L-PYROGLUTAMYL-L-HISTIDYL-L-PROLYL-BETA-ALANINAMIDE AND SALTS

This is a continuation of application Ser. No. 603,405 filed Aug. 11, 1975. Now abandoned.

DESCRIPTION OF THE INVENTION

The present invention relates to the compound L-pyroglutamyl-L-histidyl-L-prolyl-β-alaninzamide of the formula pGlu—His—Pro—NH—CH$_2$—CH$_2$—CO—NH$_2$ (I)

wherein all amino acids containing an asymmetric centre have the L-configuration, and acid addition salts thereof.

As used in this specification, the abbreviations used for the individual amino acids and their protecting groups are those hitherto commonly known and used in peptide chemistry [see Schroder E. and Lubke, K.,: The Peptides, Academic Press, New York & London, Vol. I (1965) and Vol. II (1966) and IUPAC-IUB rules]. Accordingly, such abbreviations are not further defined herein, with the exception of "pGlu" which denotes pyroglutamic acid.

Examples of acid addition salts of the compound of formula I are salts with inorganic acids such as hydrochloric acid, hydrobromic acid, phosphoric acid, sulphuric acid, perchloric acid and the like and with organic acids such as acetic acid, oxalic acid, maleic acid, malic acid, tartaric acid, citric acid and the like. The pharmaceutically acceptable, non-toxic acid addition salts are especially preferred.

As used in this specification the term "lower alkyl" means a straight-chain or branched-chain hydrocarbon group containing 1-6 carbon atoms such as methyl, ethyl, propyl, isopropyl, butyl, pentyl, hexyl etc. The term "aryl" means, in particular, the phenyl group or a substituted-phenyl group. Examples of substituents which may be present on the phenyl group are, in particular, lower alkoxy, nitro and halogen (e.g. fluorine, chlorine, bromine and iodine). Examples of substituted-phenyl groups are p-nitrophenyl, tri-or penta- chlorophenyl and the like. The term "lower alkoxy" means a lower alkyloxy group in which the lower alkyl moiety has the foregoing significance (e.g. methoxy, ethoxy, propoxy, butoxy etc).

According to the process provided by the present invention, the peptide amide derivative aforesaid (i.e. the compound of formula I and its acid addition salts) are manufactured by a. reacting the dipeptide of the formula Pro—NH—CH$_2$—CH$_2$—CO—NH$_2$ (II)

with a dipeptide of the general formula pGlu—His—R$_1$ (III)

wherein R$_1$ represents a hydroxy group or a residue activating the carboxyl group,
or b. reacting a tripeptide of the general formula pGlu—His—Pro—R$_1$ (IV)

wherein R$_1$ has the significance given earlier, with the amide of the formula

NH$_2$—CH$_2$—CH$_2$—CO—NH$_2$ (V)

or c. reacting the tripeptide of the formula

His—Pro—NH—CH$_2$—CH$_2$—CO—NH$_2$ (VI)

with a compound of the general formula pGlu—R$_1$ (VII)

wherein R$_1$ has the significance given earlier,
or d. cleaving off the protecting group(s) from a tetrapeptide of the general formula R$_2$—pGlu—His(R$_3$)—Pro—NH—CH$_2$—CH$_2$—CO—NH—R$_4$ (VIII)

wherein R$_2$ represents a hydrogen atom or an amino protecting group, R$_3$ represents a hydrogen atom or a group protecting the imidazole function and R$_4$ represents a hydrogen atom or an amide protecting group, with the proviso that at least one of R$_2$, R$_3$ and R$_4$ represents other than a hydrogen atom,
or e. amidating a tetrapeptide of the general formula pGlu—His—Pro—NH—CH$_2$—CH$_2$—COX (IX)

wherein X represents a hydroxy group, a residue activating the carboxyl group or the residue —OR$_5$ in which R$_5$ represents a lower alkyl, aryl or aryl- (lower alkyl) group or the residue of a polymeric carrier material,
or f. closing the pyroglutamine ring in a tetrapeptide of the general formula R$_6$—His—Pro—NH—CH$_2$—CH$_2$—COY (X)

wherein R$_6$ represents the optionally protected glutamine or glutamic acid group, Y represents a residue activating the carboxyl group, the residue —NHR$_4$ in which R$_4$ has the significance given earlier or the residue —OR$_5$ in which R$_5$ has the significance given earlier, with simultaneous or prior cleavage of protecting groups which may be present and, if desired, converting the compound of formula I obtained into an acid addition salt; in formulae II to X hereinbefore all amino acids containing an asymmetric centre having the L-configuration.

Examples of residues activating the carboxyl group are esters such as cyanomethyl, p-cyanophenyl, p-nitrophenyl, 2,4,5-trichlorophenyl, pentachlorophenyl, thiophenyl, p-nitrothiophenyl, 1-benztriazolyl, phthalimidyl, 1-succinimidyl, 1-piperidyl, 8-quinolyl, 5-chloro-8-quinolyl, 2-pyridyl, 2-thiopyridyl esters, azides and halides.

All protecting groups known in peptide chemistry can be used in the present invention.

Examples of amino protecting groups are those of the acyl type (e.g. formyl, benzoyl, phthalyl, trifluoroacetyl, p-tosyl, aryl- and alkylphosphoryl, phenyl- and benzylsulphonyl, tritylsulphenyl, o-initrophenylsulphenyl, γ-chlorobutyryl and o-nitrophenoxyacetyl), of the alkyl type (e.g. trityl, benzyl, alkylidene) or of the urethane type (e.g. carbobenzoxy, p-bromo-, p-chloro- or p-methoxycarbobenzoxy, tolyloxy-, allyloxy-, cyclopentyloxy-, cyclohexyloxy-, t-butyloxy- or 1,1-dimethylpropyloxy-, 2-(p-biphenylyl)-2-propyloxy-carbonyl or benzylthiocarbonyl), etc.

Examples of amide protecting groups are xanthenyl, 2,4-dimethoxybenzyl, 2,4,6-trimethoxybenzyl, 4,4'-dimethoxybenzhydryl and the like.

Examples of carboxyl protecting groups are O- and S-esters (e.g. methyl, ethyl, t-butyl, benzyl, cyanomethyl, phthalimidomethyl, 4-picolyl, 2-p-tosylethyl, phenyl, p-nitrophenyl, thiophenyl and p-nitrobenzyl esters), amides or hydrazides (e.g. trityl, phenyl, carbobenzoxy and t-butoxycarbonyl hydrazides). Furthermore, the carboxyl group can be protected by salt-formation. The residue of a polymeric carrier can also be used as a carboxyl protecting group.

As special protecting groups for the histidine residue there may be mentioned, for example, benzyl, p-nitrobenzyl, tert.butoxycarbonyl, dinitrophenyl, trityl, benzyloxycarbonyl, adamantyloxycarbonyl, tosyl, piperidinocarbonyl and the like.

The reaction of the dipeptide of formula II with a dipeptide of formula III, the reaction of a tripeptide of formula IV with the amide of formula V and the reaction of the tripeptide of formula VI with a compound of formula VII can be carried out in a manner known per se. These reactions are expediently carried out in an inert organic solvent, preferably a polar organic solvent such as dimethylformamide, dimethyl sulphoxide, acetonitrile or a halogenated hydrocarbon such as dichloromethane, chloroform and the like. The reaction is also expediently carried out at a temperature below room temperature. Where $R_1$ in a dipeptide of formula III or in a tripeptide of formula IV represents the hydroxy group, the reaction is expediently carried out in the presence of a condensation agent such as dicyclohexylcarbodiimide, carbonyl-diimidazole or the like or also according to the mixed anhydride method.

The cleavage of the protecting group(s) from a tetrapeptide of formula VIII or X can be carried out in a known manner and under conditions which are relevant for the cleavage of the particular protecting group(s) present. Thus, for example, the cleavage of a benzyloxycarbonyl group can be effected by hydrogenation in the presence of a catalyst, e.g. a palladium/charcoal catalyst. The tert. butoxycarbonyl group can, for example, be removed by treatment with trifluoroacetic acid or with HCl in glacial acetic acid.

The amidation of a tetrapeptide of formula IX can be carried out in a manner known per se; preferably by reaction with ammonia at room temperature and in a suitable inert organic solvent.

The closure of the pyroglutamine ring in a tetrapeptide of formula X can be carried out in a manner known per se. Thus, for example, the ring-closure in a tetrapeptide of formula X, in which $R_6$ represents a glutamic acid residue protected with an ester group and Y represents the residue —$OR_5$, is carried out by treatment with ammonia with simultaneous cleavage of the protecting groups.

The starting materials of formulae II, VI, VIII, IX and X are novel and it will be appreciated that they also form part of the present invention. Such starting materials can be prepared in a manner known per se using customary protecting groups, especially those mentioned earlier.

The compound of formula I hereinbefore and its pharmaceutically acceptable acid addition salts possess antidepressant activity and can be used for the treatment of depressive syndromes.

The action of antidepressants can be explained by the fact that such substances normalise the activity of noradrenergic neurones in the brain, this activity being altered in the case of depressive illness. Alterations in the activity of noradrenergic neurones can be demonstrated by measuring the noradrenalin (NA) liberation; for example, by determining the concentration of endogenous NA in the brain after blocking the NA-synthesis by the dopamine β-hydroxylase inhibitor bis(4-methyl-1-homopiperazinyl-thiocarbonyl)-disulphide (FLA63). If a test substance has NA-liberating action, then this manifests itself in an intensification of the FLA63-induced NA-lowering.

In order to determine the antidepressant action of the compound of formula I hereinbefore, the lowering of NA in the entire brain of male mice was determined 90 minutes after the i.p. injection of FLA 63 (5 mg/kg). The value found after the injection of FLA 63 alone is given in the following Table as 100%. Simultaneous injection of L-pyroglutamyl-L-histidyl-L-prolyl-β-alaninamide (test substance) leads to a significant acceleration of the FLA 63-induced NA-lowering.

Table

|  | Noradrenalin (%) |
| --- | --- |
| FLA 63 alone (control) | 100.0 ± 1.2 |
| FLA 63 plus test substance | 82.2 ± 2.6 |

Accordingly, the compound of formula I increases the liberation of NA in the brain of mice. This finding, together with the observed increase in the locomotor activity in mice, are a proof of the antidepressant activity of the compound of formula I.

L-Pyroglutamyl-L-histidyl-L-prolyl-β-alaninamide of formula I has an LD 10 of above 8 g/kg p.o. and an LD 50 of above 4 g/kg i.v. in the mouse.

The dosage should be regulated according to individual requirements and can vary between 100 μg and 1 mg i.v. or from 10 to 100 mg p.o. per single dose, administered once or several times daily.

The compound of formula I and its pharmaceutically acceptable acid addition salts can be used as medicaments in the form of pharmaceutical preparations which contain them in association with a compatible pharmaceutical carrier. This carrier can be an organic or inorganic inert carrier material suitable for enteral or parenteral administration such as, for example, water, gelatine, gum arabic, lactose, starch, magnesium stearate, talc, vegetable oils, polyalkyleneglycol, petroleum jelly etc. The pharmaceutical preparations can be made up in a solid form (e.g. as tablets, dragees, suppositories or capsules) or in a liquid form (e.g. as solutions, suspensions, syrups or emulsions). The pharmaceutical preparations may be sterilised and/or may contain adjuvants such as preservatives, stabilisers, wetting agents, emulsifiers, salts for varying the osmotic pressure or buffers. Preferred administration forms are solutions (ampoules), tablets and intranasal spray solutions.

The following Examples illustrate the process provided by the present invention:

EXAMPLE I

β-alanine methyl ester hydrochloride 22 g of β-alanine were heated to reflux in 4-N HCl in methanol for 1 hour and subsequently concentrated to dryness in vacuo. This treatment was repeated a further twice and the remaining oil crystallised from methanol/ether. Yield: 27.5 g; melting point 92° C.

b. t-butyloxycarbonyl-L-prolyl-β-alanine methyl ester 17.2 g of t-butyloxycarbonyl-L-proline were dissolved in 160 ml of tetrahydrofuran, cooled to −20° C and treated with 11.1 ml of triethylamine and 7.7 ml of chloroformic acid ethyl ester. The resulting suspension was stirred at −20° C for a further 5 minutes and treated with a suspension, pre-cooled to −20° C, prepared from 13.4 g of β-alanine methyl ester hydrochloride and 13.4 ml of triethylamine in 160 ml of a mixture of dimethylformamide and tetrahydrofuran (1:1). The mixture was stirred for 1 hour at a temperature below −10° C and for a further hour at room temperature, filtered and the filtrate concentrated in vacuo. The oily residue was dissolved in 200 ml of ethyl acetate and washed three times, each time with 5% potassium hydrogen sulphate solution, water, 5% sodium hydrogen carbonate solution and water, and dried over sodium sulphate. The organic phase was concentrated in vacuo and the oily residue crystallised from ether/petroleum ether. Yield: 19.2 g; melting point 70° C; $[\alpha]_D^{25} = -39.2°$ ($c = 1$ in dimethylformamide).

c. t-butyloxycarbonyl-L-prolyl-β-alaninamide

A solution of 11 g of t-butyloxycarbonyl-L-prolyl-β-alanine methyl ester in 80 ml of methanol was saturated with ammonia gas at 0° C and stored for 2 days at room temperature. The solution was concentrated in vacuo and the residue crystallised from methanol/water. Yield: 9.8 g; melting point 175°!4 177° C; $[\alpha]_D^{25} = -44.5°$ ($c = 1$ in dimethylformamide).

d. L-pyroglutamyl-L-histidyl-L-prolyl-β-alaninamide acetate

Hydrogen chloride gas was led through a solution of 9 g of t-butyloxycarbonyl-L-prolyl-β-alaninamide in 50 ml of glacial acetic acid for 1 hour, the solution concentrated in vacuo and the resulting L-prolyl-β-alaninamide hydrochloride dried overnight in vacuo.

A suspension of 7.64 g of L-pyroglutamyl-L-histidine hydrazide in a mixture of 95 ml of dimethyl sulphoxide and 125 ml of dimethylformamide was treated at −20° C with 104 ml of 1.64-N HCl in tetrahydrofuran. 5 ml of isoamyl nitrite were added to this solution. The mixture was stirred for 30 minutes at −20° C, cooled to −30° C and neutralised at this temperature with 23.7 ml of triethylamine. 7.7 g of L-prolyl-β-alaninamide hydrochloride were dissolved in a mixture of 20 ml of dimethyl sulphoxide and 15 ml of dimethylformamide. cooled to −10° C, neutralised with 4.9 ml of triethylamine and added to the previously described mixture. The thus-obtained mixture was stirred for 1 hour at −20° C, stored for 24 hours at 4° C and filtered. The filtrate was concentrated in vacuo, the residue taken up in 350 ml of water and extracted five times with 70 ml of ethyl acetate each time. The aqueous phase was concentrated in vacuo and the residue purified by countercurrent distribution in 1-butanol/glacial acetic acid/water (4:1:5). L-pyroglutamyl-L-histidyl-L-prolyl-β-alaninamide acetate was obtained by concentration of the appropriate fractions in vacuo and subsequent lyophilisation. $[\alpha]_D^{25} = -83.4°$ ($c = 1$ in 1 N acetic acid).

Optionally the residue of the ethyl acetate extraction was dissolved in 20 ml of glacial acetic acid, mixed with 30 ml of acetic acid anhydride and the mixture kept at room temperature overnight. The mixture was then diluted with 500 ml of water and concentrated to dryness in vacuo. The residue was taken up three further times in 50 ml of water each time and again evaporated to dryness. The obtained residue was then dissolved in 50 ml of water and chromatographed on an Amberlite CG-50 column (H+-Form). L-Pyroglutamyl-L-histidyl-L-prolyl-β-alaninamide was eluted with 1 N acetic acid. The respective fractions were combined and lyophilised. Paper electrophoresis: buffer from 2 ml of glacial acetic acid and 20 ml of pyridine, made up with water to 1 liter (pH 6): Rf (histidine) = 0.73 ± 0.05. Buffer from 37 ml of formic acid and 25 ml of glacial acetic acid, made up with water to 1 liter (pH = 1.7): Rf (histidine) = 0.43 ± 0.05.

EXAMPLE 2

1.1 g of benzyloxycarbonyl-β-alaninamide were hydrogenated in 25 ml of methanol with the addition of palladium/carbon. The catalyst was filtered off and the filtrate concentrated in vacuo. The residue was dissolved in 10 ml of dimethylformamide, cooled to 0° C and treated with 1.8 g of L-pyroglutamyl-L-histidyl-L-proline, 0.6 g of N-hydroxysuccinimide and 1.1 g of dicyclohexylcarbodiimide. The mixture was stirred for 24 hours at room temperature, filtered and the filtrate concentrated in vacuo. The residue was chromatographed on silica gel in chloroform/methanol/water (60:30:5). The fractions which were uniform in a thin-layer chromatogram were combined and concentrated in vacuo. The residue was dissolved in 0.1-N acetic acid and lyophilised. There were obtained 1.8 g of L-pyroglutamyl-L-histidyl-L-prolyl-β-alaninamide acetate. $[\beta]_D^{25} = -81.2°$ ($c = 1$ in 1 N acetic acid).

EXAMPLE 3 a. Benzyloxycarbonyl-β-alaninamide 111.7 g of benzyloxycarbonyl-β-alanine were dissolved in 1 liter of dimethylformamide, cooled to −20° C, treated with 70 ml of triethylamine and 67 ml of chloroformic acid isobutyl ester and stirred at −20° C for 3 minutes. Dry ammonia gas was led into this mixture until the pH rose to 11, care being taken that the temperature did not exceed −10° C. The mixture was stirred for a further 30 minutes at room temperature, filtered and the filtrate concentrated in vacuo. The residue was recrystallised from water. Yield: 91 g; melting point 162°-165° C.

b. Benzyloxycarbonyl-L-prolyl-β-alaninamide 44.5 g of benzyloxycarbonyl-β-alaninamide were hydrogenated in 250 ml of methanol with the addition of palladium/carbon. The catalyst was filtered off and the filtrate concentrated in vacuo. The residue was suspended in 100 ml of dimethylformamide and treated with 74.2 g of benzyloxycarbonyl-L-proline p-nitrophenyl ester. The mixture was stored at room temperature for 24 hours and then concentrated in vacuo. The solid residue was recrystallised from ethyl acetate. Yield: 57.8 g; melting point 151°-152° C;

$[\alpha]_D^{25} = -51.7°$ ($c = 1$ in methanol).

c. Benzyloxycarbonyl-L-histidyl-L-prolyl-β-alaninamide 11.3 g of benzyloxycarbonyl-L-prolyl-β-alaninamide were dissolved in 200 ml of methanol and hydrogenated with the addition of palladium/carbon. The catalyst was filtered off and the filtrate concentrated in vacuo. The residue was dissolved in 100 ml of dimethylformamide. A suspension of 10.7 g of benzyloxycarbonyl-L-histidine hydrazide in 150 ml of dimethylformamide was treated at −20° C with 58.7 ml of 3-N HCl in tetrahydrofuran. 6.7 ml of isoamyl nitrite were added to this solution. The mixture was stirred at −20° C for 30 minutes, cooled to −30° C, neutralised at this temperature with 24.6 ml of triethylamine and treated with the solution, pre-cooled to −20° C, of L-prolyl-$\beta$-alaninamide prepared as described earlier. The resulting mixture was stirred for 1 hour at −20° C, stored at 4° C for 24 hours and then filtered. The filtrate was concentrated in vacuo and the residue chromatographed on silica gel in chloroform/methanol (4:1). The fractions which were uniform in a thin-layer chromatogram were combined and concentrated in vacuo. The residue was crystallized from ethanol/ether. Yield: 12.9 g; Fp. 95°–97+ C. $[\alpha]_D^{25} = -40.8°$ ($c = 1$ in methanol).

d. L-pyroglutamyl-L-histidyl-L-prolyl-$\beta$-alaninamide acetate 1.0 g of benzyloxycarbonyl-L-histidyl-L-prolyl-$\beta$-alaninamide were dissolved in 50 ml of methanol and hydrogenated with the addition of palladium/carbon. The catalyst was filtered off and the filtrate concentrated in vacuo. The residue was dissolved in 10 ml of dimethylformamide and treated with 0.9 g of L-pyroglutamic acid pentachlorophenyl ester. The mixture was stored for 24 hours at room temperature and then concentrated in vacuo. The residue was dissolved in water and chromatographed on a Dowex 2 column (OH form). The fractions which were uniform in a thin-layer chromatogram were combined, acidified with acetic acid and lyophilised. Yield: 0.8 g. $[\alpha]_D^{25} = -82.2°$ ($c = 1$ in 1 N acetic acid).

EXAMPLE 4 a. Benzyloxycarbonyl-$\beta$-alaninamide 111.7 g of benzyloxycarbonyl-$\beta$-alanine were dissolved in 1 liter of dimethylformamide, cooled to −20° C, treated with 70 ml of triethylamine and 67 ml of chloroformic acid isobutyl ester and stirred at −20° C for 3 minutes. Dry ammonia gas was led into this mixture until the pH rose to 11, care being taken that the temperature did not exceed −10° C. The mixture was stirred for a further 30 minutes at room temperature, filtered and the filtrate concentrated in vacuo. The residue was recrystallised from water. Yield: 91 g; melting point 162°–165° C.

b. Benzyloxycarbonyl-L-prolyl-$\beta$-alaninamide 44.5 g of benzyloxycarbonyl-$\beta$-alaninamide were hydrogenated in 250 ml of methanol with the addition of palladium/carbon. The catalyst was filtered off and the filtrate concentrated in vacuo. The residue was suspended in 100 ml of dimethylformamide and treated with 14.2 g of benyloxycarbonxyl-L-proline p-nitrophenyl ester. The mixture was stored for 24 hours at room temperature and then concentrated in vacuo. The solid residue was recrystallised from ethyl acetate. Yield: 57.8 g; melting point 151°–152° C; $[\alpha]_D^{25} = -51.7°$ ($c = 1$ in methanol).

c. Benzyloxycarbonyl-L-histidyl-L-prolyl-$\beta$-alaninamide 11.3 g of benzyloxycarbonyl-L-prolyl-$\beta$-alaninamide were dissolved in 200 ml of methanol and hydrogenated with the addition of palladium/carbon. The catalyst was filtered off and the filtrate concentrated in vacuo. The residue was dissolved in 100 ml of dimethylformamide. A suspension of 10.7 g of benzyloxycarbonyl-L-histidine hydrazide in 150 ml of dimethylformamide was treated at −20° C with 58.7 ml of 3-N HCl in tetrahydrofuran. 6.7 ml of isoamyl nitrite were added to this solution. The mixture was stirred at −20° C for 30 minutes, cooled to −30° C, neutralised at this temperature with 24.6 ml of triethylamine and treated with the solution, pre-cooled to −20° C, of L-prolyl-$\beta$-alaninamide prepared as described earlier. The resulting mixture was stirred at −20 C for 1 hour, stored for 24 hours at 4° C and filtered. The filtrate was concentrated in vacuo and the residue chromatographed on silica gel in chloroform/methanol (4:1). The fractions which were uniform in a thin-layer chromatogram were combined and concentrated in vacuo. The residue was crystallized from ethanol/ether. Yield: 12.9 g; Fp. 95°–97° C. $[\alpha]_D^{25} = -40.8°$ ($c = 1$ in methanol).

d. Benzyloxycarbonyl-L-pyroglutamyl-L-histidyl-L-prolyl-$\beta$-alaninamide hemiacetate 1.0 g of benzyloxycarbonyl-L-histidyl-L-prolyl-$\beta$-alaninamide were dissolved in 50 ml of methanol and hydrogenated with the addition of palladium/carbon. The catalyst was filtered off and the filtrate concentrated in vacuo. The residue was dissolved in 10 ml of dimethylformamide, cooled to 0° C and treated with 1 g of benzyloxycarbonyl-L-pyroglutamic acid p-nitrophenyl ester. The solution was stored at room temperature for 24 hours and then concentrated in vacuo. The residue was dissolved in a mixture of chloroform/methanol/glacial acetic acid (95:5:3) and added to a silica gel column. The column was firstly washed with the aforementioned mixture and then the desired peptide was eluted using chloroform/methanol/water (60:30:5). The fractions which were uniform in a thin-layer chromatogram were combined and concentrated in vacuo. The residue was dissolved in 50 ml of water and lyophilised. Yield: 0.9 g; $[\alpha]_D^{25} = -11.0°$ ($c = 1$ in 1-N acetic acid).

e. L-pyroglutamyl-L-histidyl-L-prolyl-$\beta$-alaninamide acetate 100 mg of benzyloxycarbonyl-L-pyroglutamyl-L-histidyl-L-prolyl-$\beta$-alaninamide hemiacetate were dissolved in 20 ml of 0.5-N acetic acid and hydrogenated with the addition of palladium/carbon. The catalyst was filtered off and the filtrate lyophilised. Yield: 80 mg.

$[\alpha]_D^{25} = -82.5°$ ($c = 1$ in 1 N acetic acid).

EXAMPLE 5 a. Benzyloxycarbonyl-L-prolyl-$\beta$-alanine methyl ester 24.9 g of benzyloxycarbonyl-L-proline were dissolved in 200 ml of dimethylformamide, cooled to −20° C and treated with 11.1 ml of N-methylmorpholine and 13.0 ml of chloroformic acid isobutyl ester. The suspension was stirred for a further 2 minutes at −° C and then treated with a suspension, pre-cooled to −20° C, prepared from 14.0 g of $\beta$-alanine methyl ester hydrochloride and 11.1 ml of N-methylmorpholine in 100 ml of dimethylformamide. The mixture was stirred for 30 minutes at a temperature below −10° C and for a further 30 minutes at room temperature, filtered and the filtrate concentrated in vacuo. The oily residue was dissolved in 1.2 liters of ethyl acetate and washed three times, each time with 1-N hydrochloric acid, water, 10% sodium carbonate solution and saturated sodium chloride solution, and dried over sodium sulphate. The organic phase was concentrated in vacuo and the oily residue crystallised from ethyl acetate/hexane. Yield: 22.8 g; melting point 55° C; $[\alpha]_D^{25} = -50.7°$ ($c = 1$ in methanol).

b. L-pyroglutamyl-L-histidyl-L-prolyl-β-alanine methyl ester acetate 10.0 g of benzyloxycarbonyl-L-prolyl-β-alanine methyl ester were dissolved in 50 ml of methanol and hydrogenated with the addition of palladium/carbon. The catalyst was filtered off and the filtrate concentrated in vacuo. The L-prolyl-β-alanine methyl ester obtained as the residue was dissolved in 20 ml of dimethylformamide and reacted with L-pyroglutamyl-L-histidine azide (prepared from 8.4 g of L-pyroglutamyl-L-histidine hydrazide). The mixture was stirred at −20° C for 1 hour, stored at 4° C for 24 hours and then filtered. The filtrate was concentrated in vacuo, the residue taken up in 250 ml of water and extracted five times with 100 ml of ethyl acetate each time. The aqueous phase was added to a Dowex 50W (H form) column (3 × 35 cm), the column was washed with 1 liter of water and the product eluted with a buffer consisting of pyridine/glacial acetic acid/water (150:20:330). The fractions containing the product were diluted with water, adjusted to pH 5 with acetic acid, concentrated in vacuo, again diluted with water and then lyophilised. The lyophilisate was chromatographed on silica gel using chloroform/methanol/water (60:30:5). The fractions which were uniform in a thin-layer chromatogram were combined and concentrated in vacuo. The residue was dissolved in 200 ml of water and lyophilised. Yield: 8.7 g; $[\alpha]_D^{25} = -82.8°$ ($c = 1$ in 1-N acetic acid).

c. L-pyroglutamyl-l-histidyl-l-prolyl-β-alaninamide 1.0 g of L-pyroglutamyl-L-histidyl-L-prolyl-β-alanine methyl ester acetate was dissolved in 100 ml of methanol. The resulting solution was saturated with ammonia at 0° C, the vessel was made gas-tight and stored at room temperature for 3 days. The solution was then concentrated in vacuo, the residue dissolved in 50 ml of water and lyophilised. Yield: 900 mg. $[\alpha]_D^{25} = -94.9°$ ($c = 1$ in 1 N acetic acid).

EXAMPLE 6

Scored tablets having the following composition are manufactured in the usual manner:

Table

| | |
|---|---|
| L-pyroglutamyl-L-histidyl-L-prolyl-β-alaninamide acetate | 22.77 mg |
| Maize starch | 80.00 mg |
| Lactose | 67.23 mg |
| Precipitated silicic acid | 20.00 mg |
| Polyvinylpyrrolidone | 6.00 mg |
| Talc | 3.60 mg |
| Magnesium stearate | 0.40 mg |

Table -continued

| | |
|---|---|
| | 200.00 mg |

EXAMPLE 7

Ampoule solutions having the following composition are manufactured in the usual manner:

| | | | |
|---|---|---|---|
| a) | L-pyroglutamyl-L-histidyl-L-prolyl-β-alaninamide acetate | 0.227 | mg |
| | Mannitol | 0.1 | g |
| | Water for injection ad | 2.0 | ml |
| b) | L-pyroglutamyl-L-histidyl-L-prolyl-β-alaninamide acetate | 0.569 | mg |
| | Mannitol | 0.1 | g |
| | Water for injection ad | 2.0 | ml |

We claim:

1. L-Pyroglutamyl-L-histidyl-L-prolyl-beta-alaninamide and acid addition salts thereof.

2. A dipeptide of the formula $$\text{Pro—NH—CH}_2\text{—CH}_2\text{—CO—NH}_2 \qquad \text{(II)}$$

wherein the proline has the L-configuration.

3. A tripeptide of the formula $$\text{His—Pro—NH—CH}_2\text{—CH}_2\text{—CO—NH}_2 \qquad \text{(VI)}$$

wherein the amino acids containing an asymmetric center have the L-configuration.

4. A tetrapeptide of the formula $$R_2\text{—pGlu—His}(R_3)\text{—Pro—NH—CH}_2\text{—CH}_2\text{—CO—NH—R}_4 \qquad \text{(VIII)}$$

wherein $R_2$ is hydrogen or an amino protecting group, $R_3$ is hydrogen or a group protecting the imidazole function and $R_4$ is hydrogen or an amide protecting group, with the proviso that at least one of $4_2$, $R_2$ and $R_4$ represents other than hydrogen and the amino acids containing as asymmetric center have the L-configuration.

5. A tetrapeptide of the formula $$\text{pGlu—His—Pro—NH—CH}_2\text{—CH}_2\text{—COX} \qquad \text{(IX)}$$

wherein X is hydroxy, a residue activating the carboxyl group or the residue —$OR_5$ in which $R_5$ is lower alkyl, aryl, aryl-(lower alkyl) or the residue of a polymeric carrier material and wherein the amino acids containing an asymmetric center have the L-configuration.

6. A tetrapeptide of the general formula $$R_6\text{—His—Pro—NH—CH}_2\text{—CH}_2\text{—COY} \qquad \text{(X)}$$

wherein $R_6$ is glutamine or glutamic acid residue which may be in protected form, Y is a residue activating the carboxyl group, the residue—$NHR_4$, in which $R_4$ is hydrogen or an amide protecting group, or the residue —$OR_5$, in which $R_5$ is lower alkyl, aryl, aryl-(lower alkyl) or the residue of a polymeric carrier material, and wherein the amino acids containing an asymmetric center have the L-configuration.

* * * * *